US00PP24391P2

(12) United States Plant Patent
Williams

(10) Patent No.: US PP24,391 P2
(45) Date of Patent: Apr. 15, 2014

(54) ***ALOCASIA* PLANT NAMED 'UPRIGHT MAYAN MASK'**

(50) Latin Name: ***Alocasia* hybrid**
Varietal Denomination: Upright Mayan Mask

(75) Inventor: Brian Paul Williams, Louisville, KY (US)

(73) Assignee: Brian's Botanicals, Louisville, KY (US)

( * ) Notice: Subject to any disclaimer, the term of this patent is extended or adjusted under 35 U.S.C. 154(b) by 118 days.

(21) Appl. No.: 13/385,942

(22) Filed: Mar. 14, 2012

(51) Int. Cl.
*A01H 5/00* (2006.01)

(52) U.S. Cl.
USPC ..... Plt./373

(58) Field of Classification Search
USPC ..... Plt./263.1, 373
See application file for complete search history.

(56) References Cited

PUBLICATIONS

Plants, Nouveau, *Alocasia* 'Mayan Mask' PPAF (http://www.plantsnouveau.com/plant/alocasia-mayan-mask/ [Aug. 28, 2013, 1:26:05PM], 2 pages.*

* cited by examiner

*Primary Examiner* — Howard Locker
(74) *Attorney, Agent, or Firm* — Penny J. Aguirre

(57) ABSTRACT

A new cultivar of *Alocasia* plant named 'Upright Mayan Mask', that is characterized by its leaves that are 1 to 3 feet in length (age dependant), dark green in color with lighter green veins on the upper surface and dark purple in color on the lower surface with colors non-fading with sunlight and age, its leaves that are thick and durable that remain upright with age and are wind tolerant, its light green petioles, its upright plant habit providing good cold tolerance and rot resistance, its ability to produce large stem-like tubers with age, its fast growth rate, its healthy root system, and its height of about 1.8 m.

3 Drawing Sheets

Botanical classification: *Alocasia* hybrid.
Cultivar designation: 'Upright Mayan Mask'.

BACKGROUND OF THE INVENTION

The present invention, *Alocasia* 'Upright Mayan Mask', relates to a new and distinct interspecific hybrid of *Alocasia*, hereinafter referred to by its cultivar name, 'Upright Mayan Mask'. 'Upright Mayan Mask' is a new tropical plant used as a landscape and container plant in tropical and subtropical areas.

The new cultivar was derived from a controlled breeding program conducted by the Inventor at his nursery in Louisville, Ky. The overall purpose of the breeding program is to make selections of *Alocasia* plants with large, colorful leaves that are easy to grow in the nursery and landscape. 'Upright Mayan Mask' arose from a cross made in July of 2008 between an unnamed plant of *Alocaisia odora* as the female parent and an unnamed plant of *Alocasia amazonica* as the male parent. 'Upright Mayan Mask' was selected as a single unique plant in April of 2010 from amongst the seedlings derived from the above cross.

Asexual propagation of the new cultivar was first accomplished by in vitro propagation under the direction of the Inventor in Eustis, Fla. in June of 2007. Asexual propagation by in vitro propagation and rhizome division of the new cultivar has shown that the unique features of 'Upright Mayan Mask' are stable and reproduced true to type in successive generations.

SUMMARY OF THE INVENTION

The following traits have been repeatedly observed and represent the characteristics of the new cultivar. These attributes in combination distinguish 'Upright Mayan Mask' as a new and unique cultivar of *Alocasia*.

1. 'Upright Mayan Mask' exhibits upright leaves that are 1 to 3 feet in length (age dependant), dark green in color with lighter green veins on the upper surface, and dark purple in color on the lower surface.
2. 'Upright Mayan Mask' exhibits leaves that fade very little with age and sun exposure.
3. 'Upright Mayan Mask' exhibits leaves that are thick and durable; leaves are wind tolerant and remain upright with age.
4. 'Upright Mayan Mask' exhibits petioles that are light green in color.
5. 'Upright Mayan Mask' exhibits an upright plant habit providing more cold tolerance and rot resistance.
6. 'Upright Mayan Mask' exhibits a healthy root system.
7. 'Upright Mayan Mask' can produce large tuber-like trunks with age.
8. 'Upright Mayan Mask' about 1.8 m (6 feet) in height at maturity.
9. 'Upright Mayan Mask' exhibits a fast growth rate and produces a marketable plant in less than time than for many other *Alocasia* cultivars.

The female parent of 'Upright Mayan Mask', an unnamed plant of *A. odora* differs from 'Upright Mayan Mask' in being taller in height and in having larger leaves that are green on both surfaces and have larger veins. The male parent of 'Upright Mayan Mask', an unnamed plant of *A. amazonia* differs from 'Upright Mayan Mask' in having shorter leaves with upper surfaces that are dark green with white veins and leaf tips that point downward, in being shorter in height, and in being more sensitive to cold and root rot. 'Upright Mayan Mask' can be most closely compared to the cultivars 'Mayan Mask' (not patented) and 'Borneo Giant' (not patented).

'Mayan Mask' is similar to 'Upright Mayan Mask' in having thick leaves that are green with light green veins on the upper surface and purple on the lower surface. 'Mayan Mask' differs from 'Upright Mayan Mask' in being shorter in height, in having smaller leaves that are more rounded in shape, in being held less upright as the plant ages, and with lower surfaces that are less colorfast. 'Borneo Giant' is similar to 'Upright Mayan Mask' in having foliage that is held upright. 'Borneo Giant' differs from 'Upright Mayan Mask' in having a larger plant size, in having a slower growth rate when young, and in having leaves that are larger and green on both surfaces.

BRIEF DESCRIPTION OF THE DRAWING

The accompanying colored photographs illustrate the overall appearance and distinct characteristics of the new *Alocasia*, 'Upright Mayan Mask'. The photographs were taken of a 1 year-old plant of 'Upright Mayan Mask' as grown outdoors in a 2-gallon container under 6 mm poly and natural lighting in Louisville, Ky.

Figure 1:
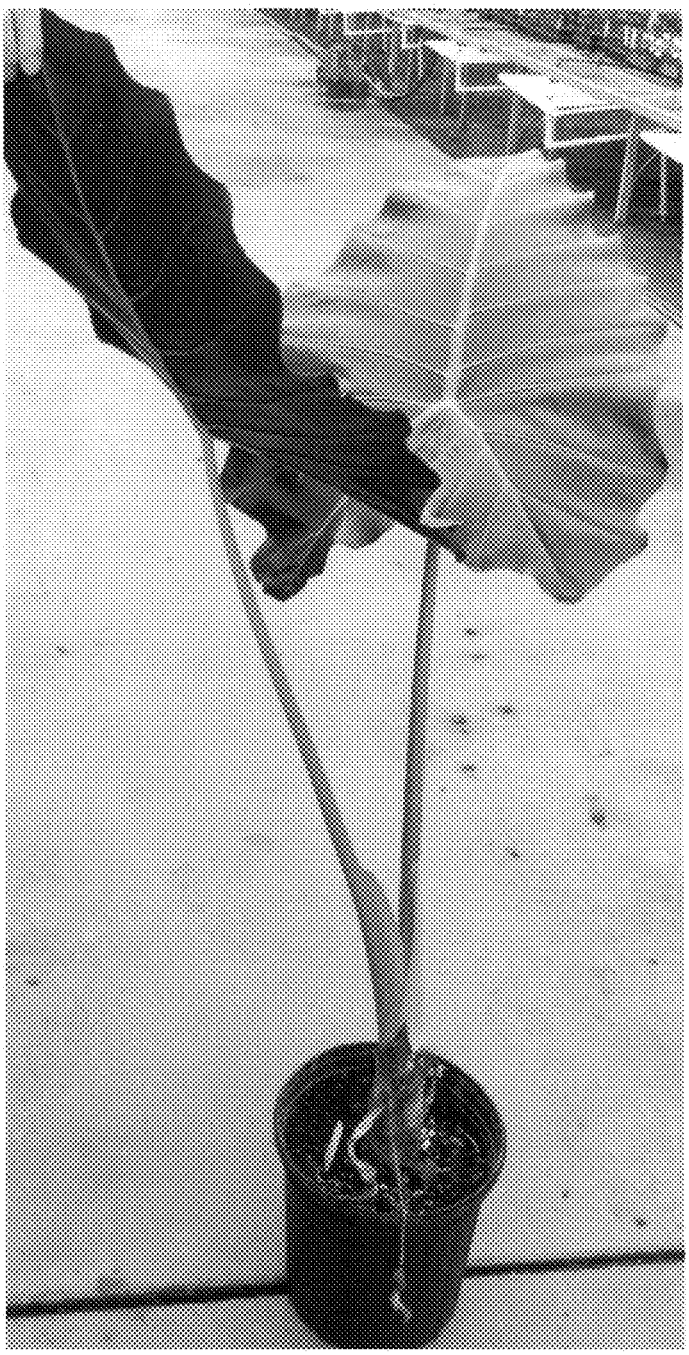
FIG. 1 provides an overall view of the foliage and plant habit of 'Upright Mayan Mask'.
Figure 2:
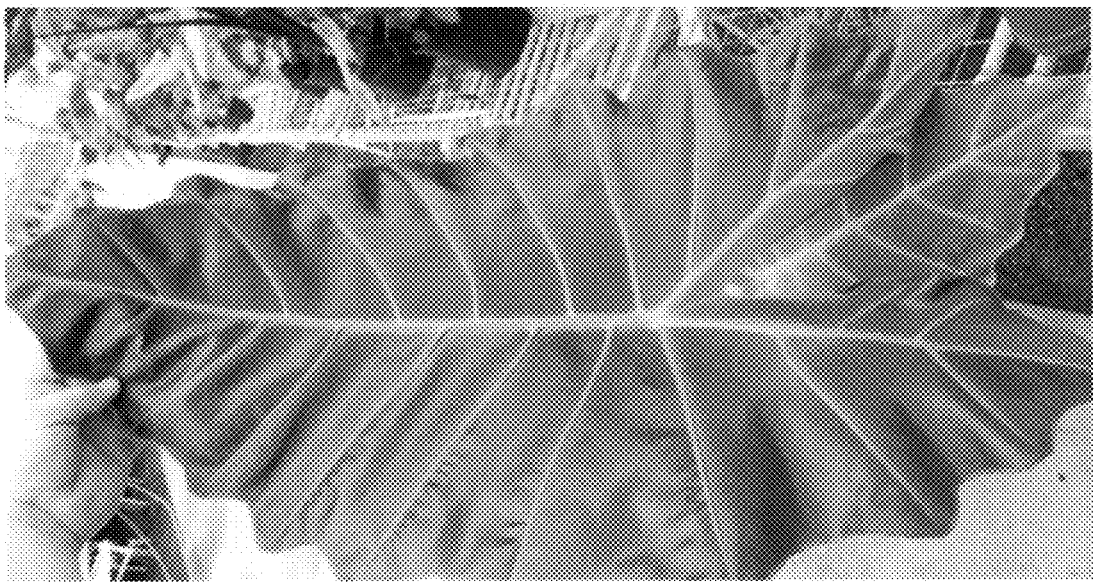

The photograph in FIG. 2 provides a close-up view of the upper surface of a leaf of 'Upright Mayan Mask'.

Figure 3:
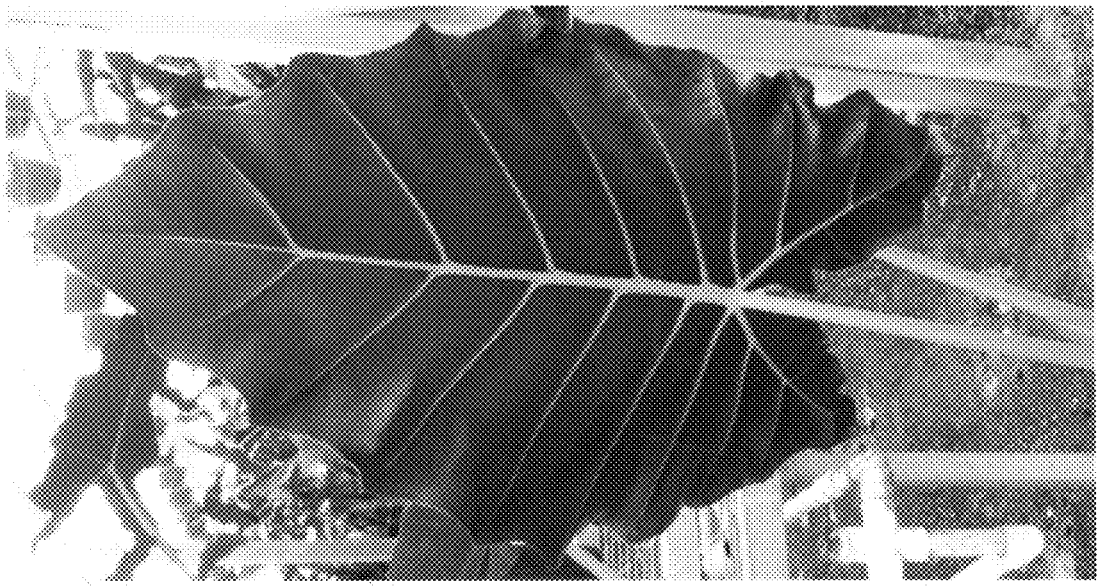

The photograph in FIG. 3 provides a close-up view of the lower surface of a leaf of 'Upright Mayan Mask'.

Figure 4:
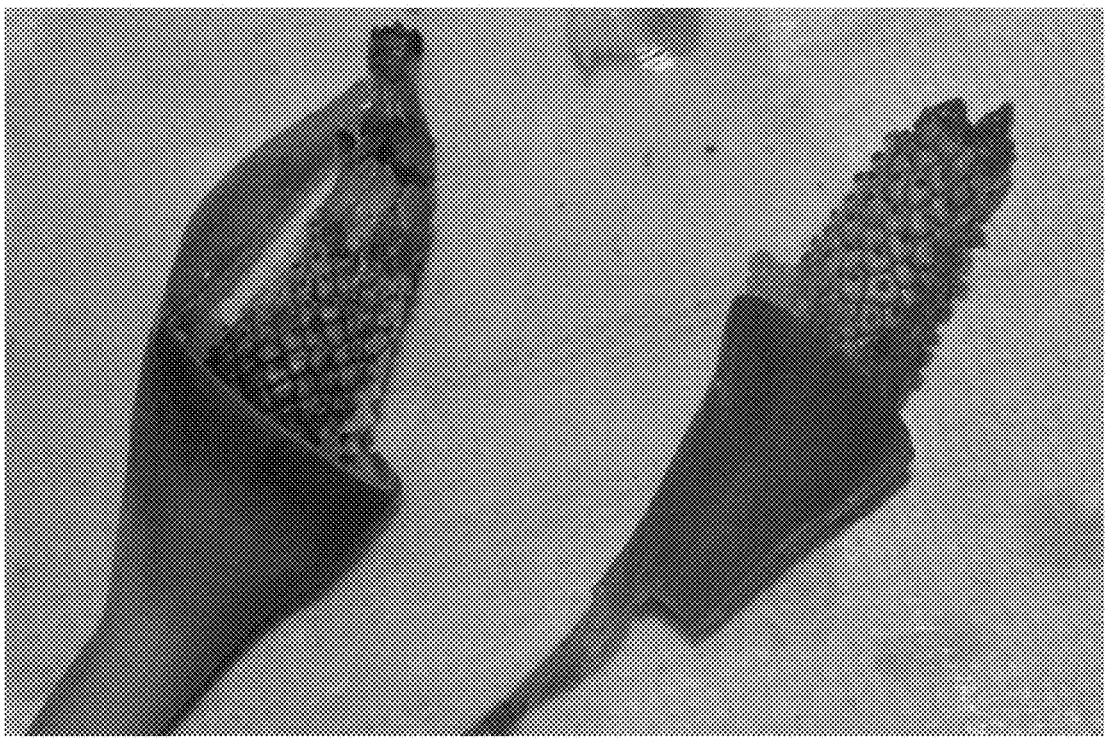

The photograph in FIG. 4 provides a view of the undeveloped fruit of 'Upright Mayan Mask', which rot from the apex to the base.

The colors in the photographs are as close as possible with the photographic and printing technology utilized and the color values cited in the Detailed Botanical Description accurately describe the colors of the new *Alocasia*.

DETAILED BOTANICAL DESCRIPTION OF THE PLANT

The following is a detailed description of three year-old plants of the new cultivar as grown outdoors in full sun under 2 mm poly greenhouse plastic in Louisville, Ky. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—April to June in Kentucky.

*Plant type.*—Tropical perennial herb.

*Plant habit.*—Upright, stemless.

*Height and spread.*—Reaches about 1.8 m in height and about 1.21 m in width.

*Hardiness.*—Tolerates temperatures of −9° C. to 48° C., defoliates at 0° C., its upright plant habit provides improved cold tolerance.

*Environmental conditions.*—Thick and durable leaves impart wind tolerance.

*Diseases and pests.*—Has shown resistance to root rot.

*Roots.*—Fleshy, healthy.

*Propagation type.*—In vitro propagation is preferred.

*Growth rate.*—Vigorous and fast, produces a marketable plant in less time than many other *Alocasia* cultivars, new leaves produced every two to five days.

*Stem description.*—Stemless, can produce tuber-like trunks with age (see petiole description).

Foliage description:

*Leaf shape.*—Cordate-sagittate.

*Leaf division.*—Single.

*Leaf base.*—Sagittate.

*Leaf apex.*—Acute.

*Leaf venation.*—Pinnate, color: upper surface; 142C, lower surface; N77C.

*Leaf margins.*—Undulate.

*Leaf attachment.*—Petiolate.

*Leaf arrangement.*—Alternate.

*Leaf surface.*—Upper surface and lower surface; coriaceous and glabrous.

*Leaf orientation.*—Upright and remains upright with age.

*Leaf color.*—New foliage: upper surface; 147A, lower surface; N77A, mature foliage: upper surface; 147B, lower surface; N78A, minimal fading as the leaf ages and with sun exposure.

*Leaf size.*—80 cm in length and 51 cm in width on plants three years in age.

*Petioles.*—Held erect to semi-erect, about 0.9 m in length and 1.3 cm in distal diameter and 3 cm in proximal diameter, glabrous surface, 143C in color, tuber-like trunk; formed at the base of the petioles with age, about 17 cm in length and 7 cm in width on a 3 year-old plant, comprised of petiole scales, surface is rough and paper-like, color is a blend of 165A and 165C.

Inflorescence description:

*Inflorescence type.*—Spadix surrounded by a spathe, male portion held above female portion, only female flowers were developed.

*Inflorescence size.*—Average of 22 cm in length and 4 cm in diameter.

*Inflorescence bud.*—Linear to slightly narrow oblanceolate in shape, an average of 16 cm in length and 1 cm in width, 143D in color.

*Flower fragrance.*—Banana fragrance.

*Lastingness of inflorescence.*—Inflorescence blooms intermittently during the bloom period, individual flowers last about 2 to 3 weeks.

*Inflorescence/flower quantity.*—Intermittent throughout the bloom season, sets of 3 or more, an average of 60 female flowers per spadix, male flowers were undeveloped.

*Spathe.*—Hooded, bract, subtending spadix, elliptic in shape, entire margin, obtuse apex, coriaceous surface, 15 cm in length and 5 cm in width, lasts 5 to 7 days, color: when opening and fully open on inner and outer rear surface; 143D, fading to 160D.

*Spadix.*—Male portion above female zone, upright cylindrical shape (phallus-like), apex narrowly pointed, about 1.3 cm in diameter (not including ovary) and 10.6 cm in length, male zone; 1.3 cm in diameter and 10.2 in length, color immature and mature 8D, female zone; 2.5 cm in diameter and length, color immature and mature 143C.

*Peduncle.*—Grows from base of plant, up to 30.5 cm in length and 1.3 cm in diameter, held at 20° angle, durable and strong, 143C in color, glabrous surface.

Reproductive organs:

*Gynoecium.*—Stigmas are 4D in color, ovary is round in shape and 143C in color.

*Androcoecium.*—Undeveloped.

*Fruit and seed.*—Fruit: develop but rot from the apex to the base and do not form see as they are sterile, fruit forms about 2 weeks after flowers; round in shape, about 2 mm in diameter, and 143C in color.

It is claimed:

1. A new and distinct cultivar of *Alocasia* plant named 'Upright Mayan Mask' as herein illustrated and described.

* * * * *